United States Patent
Kartoun et al.

(10) Patent No.: US 10,362,769 B1
(45) Date of Patent: Jul. 30, 2019

(54) SYSTEM AND METHOD FOR DETECTION OF DISEASE BREAKOUTS

(71) Applicant: International Business Machines Corporation, Armonk, NY (US)

(72) Inventors: Uri Kartoun, Cambridge, MA (US); Meenal Pore, Nairobi (KE); Fang Lu, Billerica, MA (US)

(73) Assignee: International Business Machines Corporation, Armonk, NY (US)

(*) Notice: Subject to any disclaimer, the term of this patent is extended or adjusted under 35 U.S.C. 154(b) by 0 days.

(21) Appl. No.: 15/934,120

(22) Filed: Mar. 23, 2018

(51) Int. Cl.
| | |
|---|---|
| *A01K 5/02* | (2006.01) |
| *A61B 5/00* | (2006.01) |
| *A01K 11/00* | (2006.01) |
| *A01K 29/00* | (2006.01) |
| *G16H 50/80* | (2018.01) |
| *G06Q 50/02* | (2012.01) |

(52) U.S. Cl.
CPC .............. *A01K 29/005* (2013.01); *A01K 5/02* (2013.01); *A01K 11/006* (2013.01); *A61B 5/0022* (2013.01); *G16H 50/80* (2018.01); *G06Q 50/02* (2013.01)

(58) Field of Classification Search
CPC .......... G16H 50/80; Y02A 90/24; G06F 19/30
See application file for complete search history.

(56) References Cited

U.S. PATENT DOCUMENTS

| | | | |
|---|---|---|---|
| 5,474,085 A * | 12/1995 | Hurnik ................. | A01K 11/006 119/174 |
| 6,375,612 B1 | 4/2002 | Guichon et al. | |
| 6,497,197 B1 | 12/2002 | Huisma | |
| 7,743,419 B1 * | 6/2010 | Mashevsky ........... | G06F 21/552 713/187 |
| 8,704,668 B1 | 4/2014 | Darrell et al. | |

(Continued)

FOREIGN PATENT DOCUMENTS

| | | |
|---|---|---|
| EP | 0624313 B1 | 11/1994 |
| WO | 2014068554 A1 | 5/2014 |

OTHER PUBLICATIONS

Muchiri et al., "Residents and Wild Animals Scramble to Quench Thirst at Water Points," http://www.standardmedia.co.ke/article/2000221469/residents-and-wild-animals-scramble-to-quench-thirst-at-water-points, Oct. 30, 2016, 2 pages.

(Continued)

*Primary Examiner* — Eric Blount
(74) *Attorney, Agent, or Firm* — Udi Einhorn; Ryan, Mason & Lewis, LLP (57) ABSTRACT

Methods are provided for detection of a disease breakout from a mammal population. For example, the method involves continuously receiving, from two or more sensors positioned in a mammal environment, information of a population of mammals, wherein the information received from each of the two or more sensors is in a different data format; comparing the received information of the population of mammals or other animals with known disease symptom information; and in response to determining that the information of the population of mammals exceeds a pre-determined threshold alert level, generating an alert to prevent or control the disease; wherein the steps of the method are performed in accordance with a processor and a memory.

20 Claims, 5 Drawing Sheets

(56) References Cited

U.S. PATENT DOCUMENTS

| | | | | |
|---|---|---|---|---|
| 9,746,985 | B1* | 8/2017 | Humayun | G06F 17/30672 |
| 9,905,133 | B1* | 2/2018 | Kumar | G05D 1/0088 |
| 2002/0010390 | A1* | 1/2002 | Guice | A01K 11/008 600/300 |
| 2006/0036619 | A1* | 2/2006 | Fuerst | G06Q 10/10 |
| 2007/0037231 | A1 | 2/2007 | Sauer-Budge et al. | |
| 2009/0312660 | A1 | 12/2009 | Guarino et al. | |
| 2010/0175006 | A1 | 7/2010 | Li | |
| 2010/0198023 | A1* | 8/2010 | Yanai | G06F 19/3418 600/301 |
| 2010/0198024 | A1* | 8/2010 | Elazari-Volcani | G16H 10/60 600/301 |
| 2011/0093249 | A1 | 4/2011 | Holmes et al. | |
| 2012/0197896 | A1* | 8/2012 | Li | H04L 29/08072 707/740 |
| 2013/0318027 | A1* | 11/2013 | Almogy | G16H 50/80 706/52 |
| 2014/0293749 | A1 | 10/2014 | Gervaise | |
| 2016/0132652 | A1 | 5/2016 | Chapman Bates et al. | |
| 2016/0210559 | A1* | 7/2016 | Jean-Baptiste | G06F 19/30 |
| 2017/0369167 | A1* | 12/2017 | Meadow | B64D 1/02 |

OTHER PUBLICATIONS

D.L. Coppock et al., "For Pastoralists the Risk May Be in the Drinking Water: The Case of Kargi, N. Kenya," Global Livestock Collaborative Research Support Program, May 2003, 4 pages.

United Nations Office for the Coordinate of Human Affairs, "Pastoralists Living on the Edge of Existence in Kenya," Aug. 2008, 4 pages.

Yale News, Yale Scientists Find Evidence Healthy Animals Detect and Avoid Sick Animals, http://news.yale.edu/1999/09/21/yale-scientists-find-evidence-healthy-animals-detect-and-avoid-sick-animals, Sep. 21, 1999, 2 pages.

M. Doucleff, "The Camel Did It: Scientists Nail Down Source of Middle East Virus," http://www.npr.org/sections/health-shots/2014/06/04/318851265/the-camel-did-it-scientists-nail-down-source-of-middle-east-virus, Jun. 4, 2014, 5 pages.

Rain Forest Connection "Our Work: Prevent Illegal Deforestation," http://rfcx.org/about, 2017, 2 pages.

Somerville College, "Stephen Roberts interviewed by BBC Radio Oxford about how a £500,000 Google Impact Prize Will Aid Mosquito Research," http://www.some.ox.ac.uk/news/stephen-roberts-interviewed-by-bbc-radio-oxford-about-how-a-500000-google-impact-prize-will-aid-mosquito-research, Aug. 7, 2014, 1 page.

M. Harris, "A Web of Sensors Enfolds an Entire Forest to Uncover Clues to Climate Change," http://spectrum.ieee.org/green-tech/conservation/a-web-of-sensors-enfolds-an-entire-forest-to-uncover-clues-to-climate-change, Feb. 26, 2015, 14 pages.

D.K. Mellinger, "A method for detecting whistles, moans, and other frequency contour sounds," The Journal of the Acoustical Society of America, https://www.ncbi.nlm.nih.gov/pubmed/21682426, Jun. 2011, 7 pages, vol. 129, No. 6.

V. Exadaktylos, et al., "Automatic Identification and Interpretation of Animal Sounds, Application to Livestock Production Optimisation," "Soundscape Semiotics—Localization and Categorization," 2014, pp. 65-81, Intech.

E. Lynch, et al., "The Use of On-Animal Acoustical Recording Devices for Studying Animal Behavior," Ecology and Evolution 2013, pp. 2030-2037, vol. 3, No. 7.

Y. Chung, et al., "Automatic Detection and Recognition of Pig Wasting Diseases Using Sound Data in Audio Surveillance Systems," Sensors, 2013, pp. 12929-12942, vol. 13, No. 10.

S. Neethirajan, et al., "Recent Advancement in Biosensors Technology for Animal and Livestock Health Management," https://www.biorxiv.org/content/early/2017/04/19/128504, Apr. 19, 2017, 82 pages.

S. Alasaad, et al., "The Use of Radio-Collars for Monitoring Wildlife Diseases: A Case Study from Iberian Ibex Affected by Sarcoptes Scabiei in Sierra Nevada, Spain." Parasites & Vectors, 2013, vol. 6, No. 242.

R. N. Handcock, et al., "Monitoring Animal Behaviour and Environmental Interactions Using Wireless Sensor Networks, GPS Collars and Satellite Remote Sensing", Sensors, 2009, pp. 3586-3603, vol. 9, No. 5.

T. Mörner, et al., "Surveillance Monitoring of Wildlife Diseases." Revue Scientifique Et Technique, 2002, pp. 67-76, vol. 21, No. 1.

Anonymous, "A Method and System for Predicting Propagation Path of a Disease." IP.com Disclosure No. IPCOM000245155D, Feb. 14, 2016, 5 pages.

R. Maciejewski, et al., "LAHVA: Linked Animal-Human Health Visual Analytics," IEEE Symposium on Visual Analytics Science and Technology, 2007, pp. 27-34.

* cited by examiner

SYSTEM AND METHOD FOR DETECTION OF DISEASE BREAKOUTS

BACKGROUND

This disclosure generally relates to a system and method for the detection of disease breakouts from a mammal population.

Airborne virus and bacterial diseases represent a major hazard to organisms with lungs such as mammals including humans and animals. There are certain diseases that could spread across wild and domestic animals and then further spread to humans. For example, in certain countries, many cattle farmers are pastoralists and will travel long distances with their cattle herds looking for food and water. Since these countries are badly affected by droughts, the authorities often put in cattle watering points along their travel routes. These watering points are a place where human and cattle can come into contact. In Africa, tuberculosis in cattle (known as bovine TB) is still common and can be spread, for example, between cattle through droplets in the air or to humans through unpasteurized milk from the cattle. One of the symptoms of bovine TB is coughing. Animals and the humans have little or no ultimate protection against airborne disease.

SUMMARY

Embodiments described herein provide a system and method for detection of disease breakouts from a mammal population.

For example, one exemplary embodiment includes a method for detection of a disease breakout from a mammal population comprising:

continuously receiving, from two or more sensors positioned in a mammal environment, information of a population of mammals, wherein the information received from each of the two or more sensors is in a different data format;

comparing the received information of the population of mammals with known disease symptom information; and in response to determining that the information of the population of mammals is a known disease symptom, generating an alert to prevent or control the disease;

wherein the steps of the method are performed in accordance with a processor and a memory.

Another exemplary embodiment includes a system for detection of a disease breakout from a mammal population which comprises: a memory and a processor. The processor is operatively coupled to the memory and configured to implement the steps of:

continuously receiving, from two or more sensors positioned in a mammal environment, information of a population of mammals, wherein the information received from each of the two or more sensors is in a different data format;

comparing the received information of the population of mammals with known disease symptom information; and in response to determining that the information of the population of mammals is a known disease symptom, generating an alert to prevent or control the disease.

Another exemplary embodiment includes a computer program product comprising a computer readable storage medium for storing computer readable program code which, when executed, causes a computer to:

continuously receive, from two or more sensors positioned in a mammal environment, information of a population of mammals, wherein the information received from each of the two or more sensors is in a different data format;

comparing the received information of the population of mammals with known disease symptom information; and in response to determining that the information of the population of mammals is a known disease symptom, generating an alert to prevent or control the disease.

These and other features, objects and advantages of the present invention will become apparent from the following detailed description of illustrative embodiments thereof, which is to be read in connection with the accompanying drawings.

DETAILED DESCRIPTION

Embodiments of the present invention will now be described in further detail with regard to systems and methods for the early detection of disease breakouts. For example, as multiple pastoralists use a single water source for their animals such as cattle, there may be an increase in the risk of transmission of disease from (a) wild animals to domestic livestock and humans, (b) from livestock to humans, and (c) between livestock. Embodiments of the present invention describe a system and a method that, in real-time, monitors, at least an audio and one other detection factor such as motion of a population of mammals to determine symptom and/or disease information. The term "mammal" as used herein refers to humans and animals, e.g., cattle, sheep, pigs, goats, buffalo, camels, birds and fish. However, one skilled in the art will understand that the system and method herein can include any type of animal. Accordingly, features of the embodiments of the present invention that can assist in the early detection of disease breakouts amongst mammals include, for example, detect disease breakout patterns for both animals and humans, using sensors, phones, etc., by monitoring mammal sounds, movements, and density while taking into consideration such factors as geographical, weather, and seasonal factors. The sensors can be installed at the mammals' environment (such as next to feeding locations) as well as, for instance, on trees (e.g., cameras). In addition, satellite technology enhanced with vision capabilities can also be used in the system as an optional embodiment. Further advantages of the features of the embodiments of the present invention include, for example, sending an alert, e.g., to a cell phone, to those who may be affected by the possible outbreak of the disease, and initiating a response or action to inhibit, prevent, control or remedy the outbreak of the disease, e.g. adding a chemical to a water source.

The terms "first", "second", "third" and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The term "coupled" as used herein should not be interpreted as being restricted to direct connections only. Thus, the scope of an expression such as "a first device coupled to a second device" should not be limited to devices or systems wherein an output of the first device is directly connected to an input of the second device. It should mean that there exists a path between an output of the first device and an input of the second device which may be a path including other devices or means.

Figure 1:
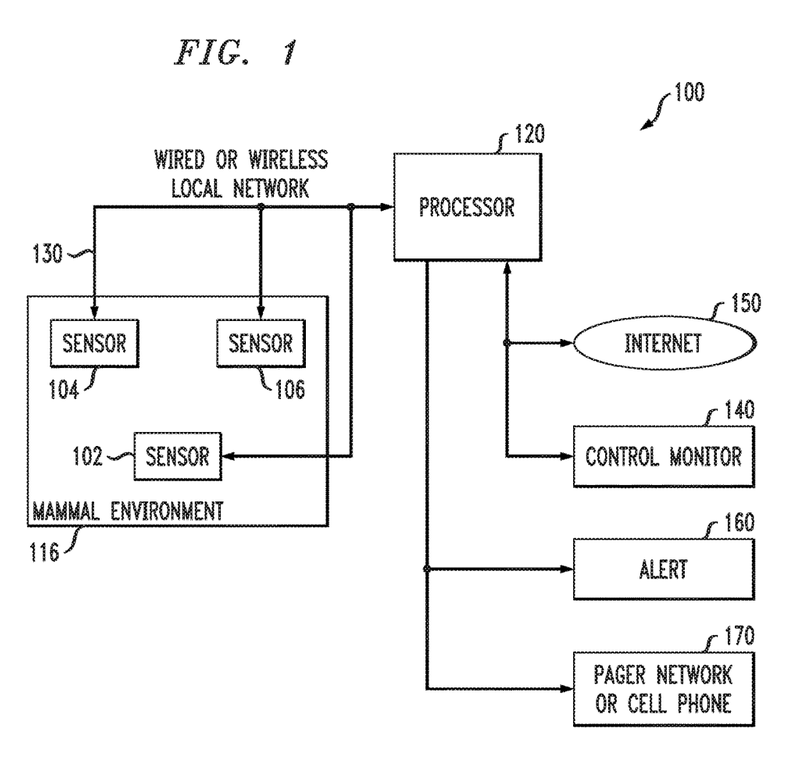
FIG. 1 is a block diagram of a system for the early detection of disease breakouts, according to an embodiment of the invention.
Figure 2:
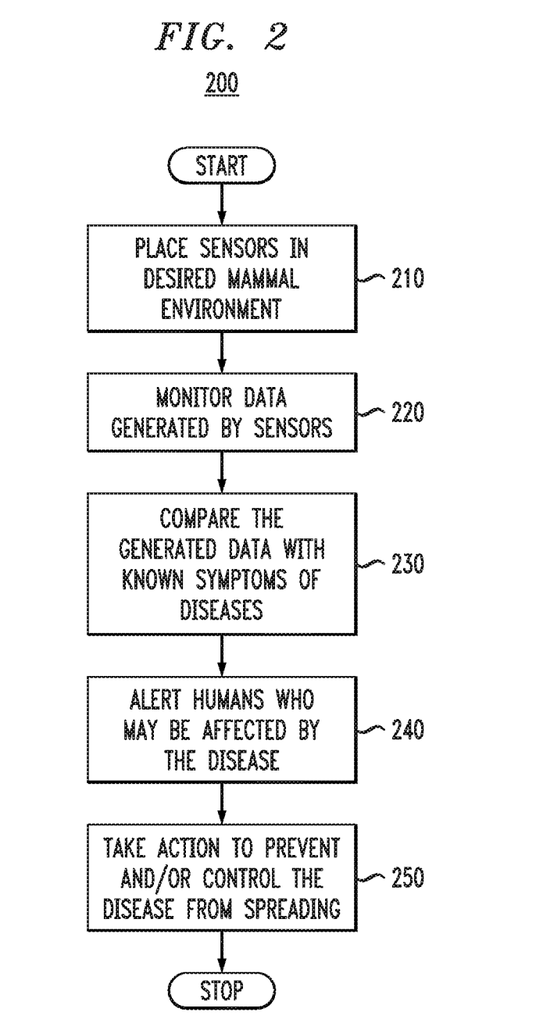
FIG. 2 is a block diagram illustrating a method for the early detection of disease breakouts, according to an embodiment of the invention.

FIGS. 1 and 2 illustrate a block diagram for a system and method for the early detection of disease breakouts, according to an embodiment of the present invention. With reference now to FIG. 1, there is a flow diagram illustrating an overview of a disease detection system 100 that can be implemented according to an embodiment of the present invention. The system 100 includes a network of sensors including, for example, sensors 102, 104 and 106 for monitoring a small or large-scale mammal environment 110. For example, sensors 102, 104 and 106 can be an audio sensor 102 and motion sensors 104 and 106. It is also contemplated that sensors 104 and 106 can be one or more video sensors (cameras), one or more image sensors, and one or more color sensors. However, one skilled in the art will understand that the number and type of sensors will vary depending on the size of the mammal environment and number of mammals being monitored.

In general, the sensors are grouped together in sensor nodes, which can have a compression, initial processing, and communications component. In one embodiment, images from an image sensor can be, for example, digitized at the sensor node and sent over a digital local network to the processing node, typically using a wireless (or wired) Ethernet network. In one embodiment, a conventional video signal can be sent over a video cable, or wireless analog video transmission device, to a processing unit, where the video is digitized. In one embodiment, a sensor can be one or more audio sensor such as, for example, one or more microphones. In one embodiment, a sensor can be one or more motion sensors such as, for example, one or more infrared sensors. Suitable infrared sensors include, for example, thermal infrared sensors. In one embodiment, a sensor can be one or more color sensors. A color sensor can measure the intensity of at least one wavelength band, in particular in the visible wavelength range, of, for example, water that is being monitored, the variable being the intensity of the wavelength band.

For example, a video sensor will allow for image analysis methods to detect the position, orientation, and pose of mammals seen in each video sensor, and this information is sent to the processor database 120. Image motion and background difference cues, and/or shape and appearance features, are employed to find regions in the image corresponding to individual mammals. These measures are then tracked over time, and compared to known models of mammal shape, appearance, and/or motion stored in the database. For example, the video or motion sensor can determine any abnormal moving patterns of the mammals. Methods using the matching of moments of inertia of an extracted shape, or using distributions of matched patches are well known to be able to accurately infer mammal type, position, pose, and orientation from video sensor observations. Both a priori models of generic mammal appearance and behavior, and models learned over time for the specific mammals being tracked, may be used for the tracking and matching process.

In the case of an audio sensor, acoustic analysis similarly compares current audio sensor measurements to a typical background model, and to models of known sounds from a priori, generic models, as well as models learned over time for the specific mammals being tracked. For example, the one or more audio sensors are used to continuously monitor the sound made by the mammals. In one embodiment, acoustic analysis as described below can determine a coughing pattern of the mammals and compare the coughing pattern to known models of certain diseases related to coughing. The system 100 can then categorize the sound behavior by different types of mammals.

An image sensor can include, for example, an acoustic imaging (sonar) sensor such as underwater-installed cameras. In this case, high resolution acoustic images can be generated using sonars with acoustic lens in place of conventional beam forming electronics. One such system is the DIDSON system available from Applied Physics Laboratory, University of Washington, 1013 NE 40th Street, Seattle, Wash. 98105.

The multimodal activity interpretation from the sensors compares the recent history of mammal position and pose, and acoustic patterns, and/or other sensor patterns, and detects unusual or interesting spatio-temporal patterns. For example, a motion sensor can continuously monitor the movement patterns made by the animals, and then calculate the animal population density at each area where they reside. Thus, the system 100 can categorize the sound and movement behavior by different types of mammals. This way, system 100 can establish a mammal specific data model to keep track of the data in order to establish a baseline of the patterns. The system 100 can be is integrated with the existing medical knowledge database where mammal related diseases information is collected and searchable.

Known techniques and methods in the computer vision and audio signal processing literature can be used to detect activities which are statistically rare, and which are known to be for a particular animal type or disease state (e.g., a particular motion pattern associated with colic in horses), or those which are previously marked as interesting (through the control monitor interface) by the operator. By using vision technologies, the system could scan specific regions to track the complexity of all measured animal characteristics in each region. For example, a fuzzy expert system which can describe, in natural language like-way, simple human or animal activity in the field of view of a surveillance camera can be used. The fuzzy system has three different components: a pre-processing module for image segmentation and feature extraction, an object identification fuzzy expert system (static model), and an action identification fuzzy expert system (dynamic temporal model). These systems are known, see, e.g., Stern et al., *A PROTOTYPE FUZZY SYSTEM FOR SURVEILLANCE PICTURE UNDERSTANDING*, International ConferenceVisualization, Imaging, and Image Processing (VIIP 2001), Marbella, Spain, Sep. 3-5, 2001. Another example of a vision technology is a system based on an ER-1 Evolution Robotics mobile robot which is a threewheeled platform equipped with an IBM ThinkPad laptop and a Logitech QuickCam Pro 4000 color camera supporting autonomous control capabilities. These systems are known, see, e.g., Kartoun et al., Vision-Based Autonomous Robot Self-Docking and Recharging, World Automation Congress (WAC) 2006, Jul. 24-26, Budapest, Hungary.

A processor 120 is connected via a wired or wireless local network 130 to audio sensor 102 and motion sensors 104 and 106 which monitor a small or large-scale mammal environment 110. The processor 120 is connected as well via a local network or digital communications channel to a control monitor 140, which is used to control system parameters and to view activity and sensor observation logs. The processor 120 is also optionally connected to the Internet 150, and the system may be controlled remotely via a web server interface. The processor is optionally connected via analog or digital signaling means to one or more alerts 160, which may be, for example, a text message, bell or light, using the protocols and signaling means of a home security system or home electronic control system. The processor is also optionally connected directly to a pager or cell phone terminal interface 170, to send a SMS or cell phone voicemail or text message. The alert 160 and the pager/phone interface 170 are used to send alert notifications to an operator; alert notifications may also be sent via standard Internet protocols using the Internet 150.

FIG. 2 is a flow diagram of an example of a method for the early detection of disease breakouts, according to an embodiment of the invention. With reference now to FIG. 2, there is a flow diagram illustrating an overview of a disease detection system 100 that can be implemented according to an embodiment of the present invention. First step 210 involves placing all the sensors, e.g., sensors 102, 104 and 106, in a suitable location for monitoring the small or large-scale mammal environment 110. For example, the sensors can be positioned in a location where a mammal lives and/or at a water source where the mammal drinks water. In one embodiment, sensors 102, 104 and 106 can be positioned in proximity to a bird's nest to monitor whether the eggs have been hatched or to track birds that migrate periodically across countries or to observe if certain birds do not properly feed their babies. In another embodiment, sensors 102, 104 and 106 can be positioned in proximity to an opening of, for example, a cave to monitor the movement of animals that may live or be located in the cave. In another embodiment, sensors 102, 104 and 106 can be positioned in proximity to water, for example, a water trough for animals, a pond, lake, etc. For example, sensors 102, 104 and 106 can be one or more microphones and one or more cameras mounted next to a water source. The system can then observe the behavior of a sample of individual animals at the water source as well as notify if a cough sound from cows may sound unusual. In addition, the recorded sound of multiple cows may indicate the potential of a spreading disease, or certain areas that used to be characterized by sound of multiple animals (such as birds, or cows) have suddenly became quiet. The system can further identify unusual sounds made by dogs, that could be an indication for rabies.

Next, step 220 in this exemplary embodiment involves monitoring the mammal environment 110 using the sensors 102, 104 and 106. In the case of using an audio sensor such as one or more microphones, this step will involve monitoring sound patterns or acoustic characteristics such as a cough or some other abnormal sound from the mammals to identify spread of a known disease. For example, one of the symptoms of bovine TB is coughing. In one embodiment, the one or more audio sensors will monitor coughing patterns of the mammals. Thus, extraction of individual sounds from a continuous recording of the sound patterns is based on the envelope of the energy of the signal and a selected (environment specific) threshold to determine if a coughing pattern exists. The underlying principle is that low amplitude noise is recorded most of the time and when a sound occurs (any sound within the mammal environment) will be recorded as a high energy signal. Whenever the amplitude of the envelope is higher than the threshold it is considered that there is a recording of a sound that needs to be identified. The mean value of the envelope over the complete recording is used for this application and experimentation suggested that it is adequate for extracting most of the signals that are of interest. The data is then transmitted to the processor 120 and control monitor 140 for storage and analysis.

In one embodiment, an additional type of sensor for collecting data would include underwater movement sensors. For example, the system according to the present invention can detect fish movement underwater to identify pollution or the spread of diseases. This can be carried out by installing counting mechanisms (such as those used to count cars crossing a junction), or underwater-installed cameras capable of identifying unusual migration of fish.

As one skilled in the art will understand, the monitoring step will also take into account environmental factors such as the time of season, temperature, dryness, geographic location, geological features, and the like. These environmental factors can assist in determining how the attributes of, for example, sound, animal density, and movement, are combined to create an accurate predictor of mammal health for a specific geography, time, and mammal.

Next, step 230 in this exemplary embodiment involves comparing the data collected and stored in the database from step 220 with known symptoms or conditions associated with a disease. For example, a historical data model can be built containing sufficient information of different symptoms or conditions associated with a disease for the different animals in the place that is being monitored. The historical data model can be continuously updated as more information is obtained. In the case of monitoring the mammals using motion sensors, it can be determined if the mammals begin to migrate from one location to another or vice versa then the system 100 can detect there is something abnormal. In addition, if the mammals' density gets higher or lower in one location but not in another then there could be a disease breakout.

The system can also provide information if the dynamics between certain regions is reasonable, i.e., not associated with an alert. For example, the densities are changing as normal, birth and death rates across regions are normal, sickness rates of animals are normal, etc. Such vision technologies could be enhanced by computational methods to process the raw data to provide a reliable determination regarding a situation in which a disease is likely to be spread.

Suitable techniques for comparing the data may include, for example, a broad selection of learning algorithms, including those that belong to supervised learning and unsupervised learning approaches. Suitable techniques may include, for example, the use of fuzzy logic, support vector machines, logistic regression, and neural networks as known in the art. In one embodiment, the system implements a machine learning algorithm such as a supervised machine learning algorithm for comparing the data. For example, a user can highlight a period of time in which no event of interest has occurred, and then highlight periods of time in which various events of interest have occurred. A machine learning algorithm can determine the distinction between each type of event semantics or lack of event semantics, and enable recognition of such events in the future based on the distinction. Similarly, a user may specify both a background time period and an event time period. The system can then learn the differentiating characteristic image semantics that sufficiently discriminate an event from a non-event, enabling the system to detect events similar to the specified event in the future. Additionally, an embodiment of the invention that implements a machine learning algorithm can also include assessing which images contributed most prominently to event detection as event-related.

The data can be compared to the known symptoms or conditions associated with a disease to determine if a predetermined threshold has been reached in order to trigger an alert as described below. For example, a predetermined threshold level can be a numerical value ranging from 0 to 1. In one embodiment, the value of the threshold can be calculated off-line by using, for example, such factors as historical sensor measurements, false disease outbreak alerts, and true disease outbreak alerts. The system 100 can continuously calculate a measure of the predetermined threshold level. If the value of the level of alertness exceeds the threshold, then the system indicates a true disease outbreak and triggers an alert.

Next, step 240 in this exemplary embodiment involves sending an alert to prevent or control the disease to an individual(s) in response to determining that the disease symptom information of the population of mammals is a known disease symptom. This can be done by means of any suitable telecommunications method of which SMS (Short Message Service), MMS, email or other information services. For example, an alert can be sent to the individuals by sending a text message, voice message, audio message, video, data and encrypted message informing the appropriate individual of the type of disease state or symptom and optionally the appropriate action to take to prevent, treat or control the disease.

Next, step 250 in this exemplary embodiment involves taking any necessary action to prevent, treat or control the condition causing the disease or the mammals affected by the disease. For example, a suitable chemical can be added to a water source that is contaminated with bacteria, such as *E. coli*. which is causing an outbreak. In another embodiment, medical equipment can be sent, e.g., by using drones, unmanned aerial vehicles (UAV), autonomous cars, mobile robots, as well as air balloons and zeppelins, to infected areas.

Figure 3:
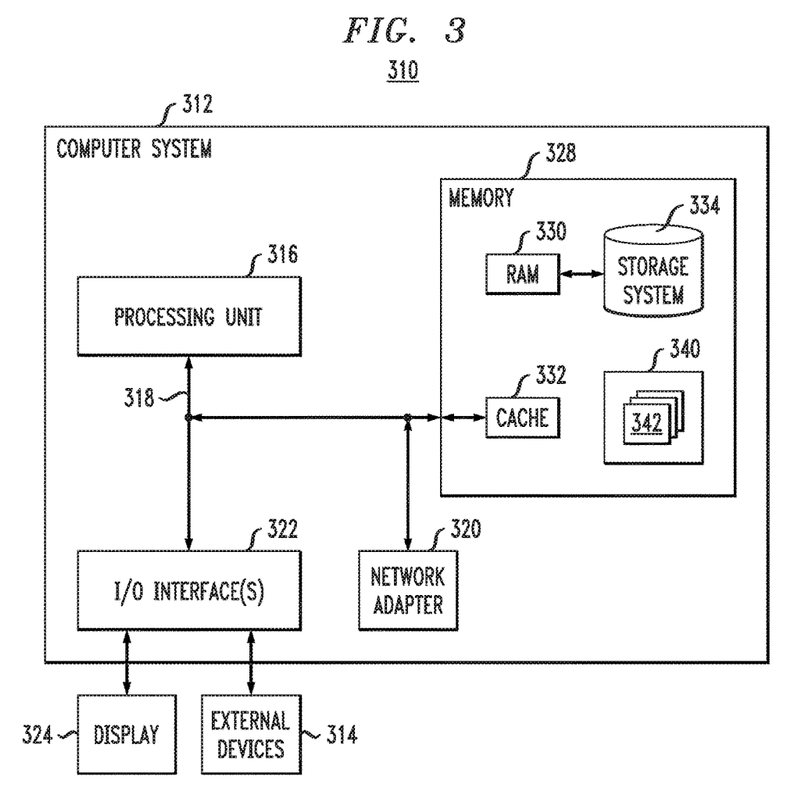
FIG. 3 depicts a computer system in accordance with which one or more components/steps of techniques of the invention which may be implemented according to an embodiment of the invention.

One or more embodiments can make use of software running on a computer or workstation. With reference to FIG. 3, in a computing node 310 there is a system/server 312, which is operational with numerous other general purpose or special purpose computing system environments or configurations. Examples of well-known computing systems, environments, and/or configurations that may be suitable for use with system/server 312 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

System/server 312 may be described in the general context of computer system executable instructions, such as program modules, being executed by a computer system. Generally, program modules may include routines, programs, objects, components, logic, data structures, and so on that perform particular tasks or implement particular abstract data types. System/server 312 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 3, system/server 312 is shown in the form of a computing device. The components of system/server 312 may include, but are not limited to, one or more processors or processing units 316, system memory 328, and bus 318 that couples various system components including system memory 328 to processor 316.

Bus 318 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

System/server 312 typically includes a variety of computer system readable media. Such media may be any available media that is accessible by system/server 312, and it includes both volatile and non-volatile media, removable and non-removable media.

The system memory 328 can include computer system readable media in the form of volatile memory, such as random access memory (RAM) 230 and/or cache memory 332. System/server 312 may further include other removable/non-removable, volatile/nonvolatile computer system storage media. By way of example only, storage system 334 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 218 by one or more data media interfaces.

As depicted and described herein, memory 328 may include at least one program product having a set (e.g., at least one) of program modules that are configured to carry out the functions of embodiments of the invention. A program/utility 340, having a set (at least one) of program modules 342, may be stored in memory 328 by way of example, and not limitation, as well as an operating system, one or more application programs, other program modules, and program data. Each of the operating system, one or more application programs, other program modules, and program data or some combination thereof, may include an implementation of a networking environment. Program modules 342 generally carry out the functions and/or methodologies of embodiments of the invention as described herein.

System/server 312 may also communicate with one or more external devices 314 such as a keyboard, a pointing device, an external data storage device (e.g., a USB drive), display 324, one or more devices that enable a user to interact with system/server 312, and/or any devices (e.g., network card, modem, etc.) that enable system/server 312 to communicate with one or more other computing devices. Such communication can occur via I/O interfaces 322. Still yet, system/server 312 can communicate with one or more networks such as a LAN, a general WAN, and/or a public network (e.g., the Internet) via network adapter 320. As depicted, network adapter 320 communicates with the other components of system/server 312 via bus 318. It should be understood that although not shown, other hardware and/or software components could be used in conjunction with system/server 312. Examples include, but are not limited to, microcode, device drivers, redundant processing units, external disk drive arrays, RAID systems, tape drives, and data archival storage systems, etc.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed. Further, embodiments of the present invention may be enhanced by using distributed computing systems such as Blockchain (e.g., to reduce likelihood for false alarms).

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 4:
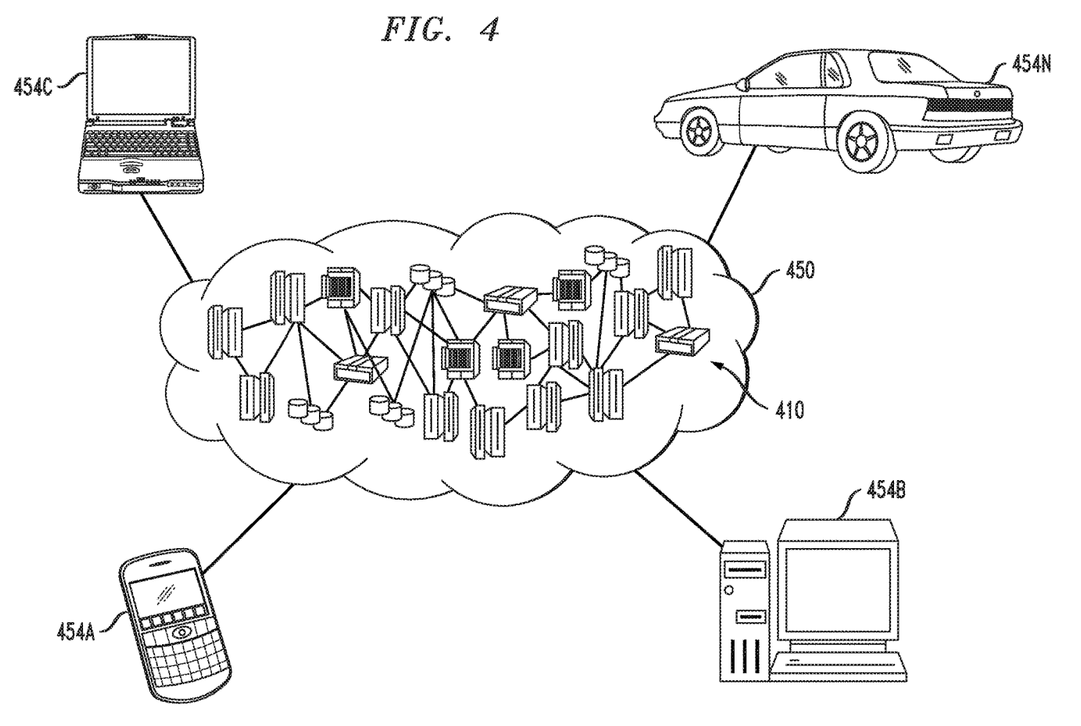
FIG. 4 depicts a cloud computing environment according to an embodiment of the invention.

Referring now to FIG. 4, illustrative cloud computing environment 450 is depicted. As shown, cloud computing environment 450 includes one or more cloud computing nodes 410 with which local computing devices used by cloud consumers, such as, for example, personal digital assistant (PDA) or cellular telephone 454A, desktop computer 454B, laptop computer 454C, and/or automobile computer system 454N may communicate. Nodes 410 may communicate with one another. They may be grouped (not shown) physically or virtually, in one or more networks, such as Private, Community, Public, or Hybrid clouds as described hereinabove, or a combination thereof. This allows cloud computing environment 450 to offer infrastructure, platforms and/or software as services for which a cloud consumer does not need to maintain resources on a local computing device. It is understood that the types of computing devices 454A-N shown in FIG. 4 are intended to be illustrative only and that computing nodes 410 and cloud computing environment 450 can communicate with any type of computerized device over any type of network and/or network addressable connection (e.g., using a web browser).

Figure 5:
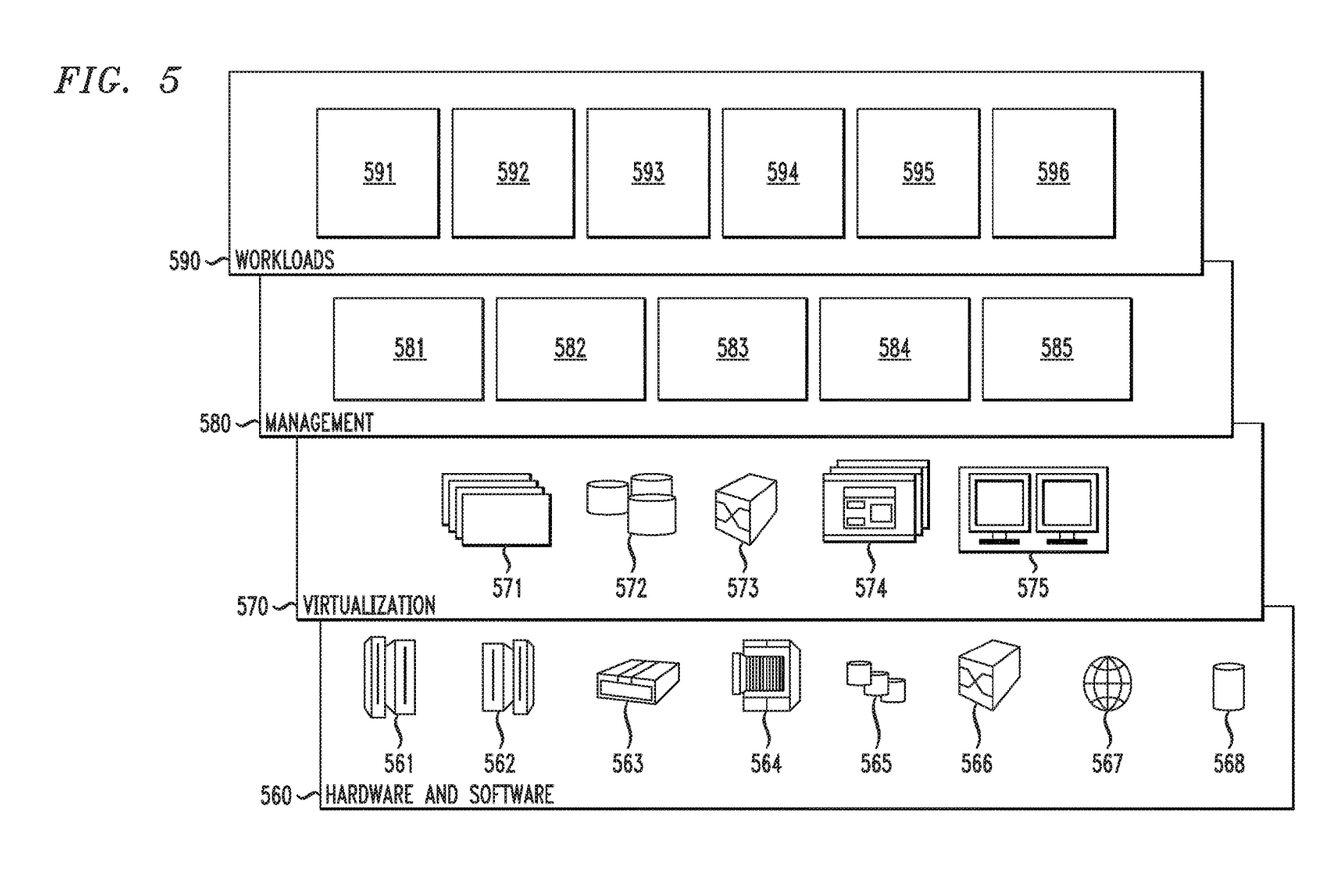
FIG. 5 depicts abstraction model layers according to an embodiment of the present invention.

Referring now to FIG. 5, a set of functional abstraction layers provided by cloud computing environment 450 (FIG. 4) is shown. It should be understood in advance that the components, layers, and functions shown in FIG. 5 are intended to be illustrative only and embodiments of the invention are not limited thereto. As depicted, the following layers and corresponding functions are provided:

Hardware and software layer 560 includes hardware and software components. Examples of hardware components include: mainframes 561; RISC (Reduced Instruction Set Computer) architecture based servers 562; servers 563; blade servers 564; storage devices 565; and networks and networking components 566. In some embodiments, software components include network application server software 567 and database software 568.

Virtualization layer 570 provides an abstraction layer from which the following examples of virtual entities may be provided: virtual servers 571; virtual storage 572; virtual networks 573, including virtual private networks; virtual applications and operating systems 574; and virtual clients 575.

In one example, management layer 580 may provide the functions described below. Resource provisioning 581 provides dynamic procurement of computing resources and other resources that are utilized to perform tasks within the cloud computing environment. Metering and Pricing 582 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 583 provides access to the cloud computing environment for consumers and system administrators. Service level management 584 provides cloud computing resource allocation and management such that required service levels are met. Service Level Agreement (SLA) planning and fulfillment 585 provide pre-arrangement for, and procurement of, cloud computing resources for which a future requirement is anticipated in accordance with an SLA.

Workloads layer 590 provides examples of functionality for which the cloud computing environment may be utilized. Examples of workloads and functions which may be provided from this layer include: transaction data capture 591; blockchain computation 592; data analytics processing 593; risk assessment 594; alert processing 595; and ameliorative/corrective/remedial action implementation 596, which may perform various functions described above.

Embodiments of the present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Embodiments of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The flowchart diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the diagrams, and combinations of blocks in the diagrams, can be implemented by special purpose hardware-based systems that perform the specified functions or acts or carry out combinations of special purpose hardware and computer instructions.

Although illustrative embodiments have been described herein with reference to the accompanying drawings, it is to be understood that the invention is not limited to those precise embodiments, and that various other changes and modifications may be made by one skilled in art without departing from the scope or spirit of the invention.

What is claimed is:

1. A method for detection of a disease breakout from a subject population comprising:
   continuously receiving, from two or more sensors positioned in a subject environment, information of a population of subjects, wherein the two or more sensors comprise one or more audio sensors and one or more motion sensors positioned along a route of travel of the subject population and one or more underwater sensors positioned in a water source located along the route of travel and wherein the information received from each of the two or more sensors is in a different data format;
   comparing the received information of the population of subjects with known disease symptom information, wherein the comparing further comprises comparing a first time period in which no event of interest has occurred to a second period of time in which one or more events of interest have occurred using a machine learning algorithm to determine a distinction between a type of event or a lack of event, and recognize a future event based on the distinction;
   in response to determining that the information of the population of subjects exceeds a pre-determined threshold alert level, generating an alert to prevent or control the disease; and
   initiating a response or action to inhibit, prevent, control or remedy the outbreak of the disease;
   wherein the steps of the method are performed in accordance with a processor and a memory.

2. The method of claim 1, wherein another of the two or more sensors is positioned in a location where the population of subjects lives, wherein the population of subjects is a population of wild animals or domestic livestock.

3. The method of claim 1, wherein the two or more sensors further comprise one or more additional sensors.

4. The method of claim 1, wherein the one or more audio sensors are one or more microphones.

5. The method of claim 3, wherein the one or more additional sensors comprise one or more of a video sensor, image sensor and color sensor.

6. The method of claim 1, wherein the step of continuously receiving comprises continuously receiving from the one or more audio sensors a coughing sound from the population of subjects.

7. The method of claim 1, wherein the step of continuously receiving comprises continuously receiving from the one or more motion sensors movement patterns of the population of subjects in order to determine any abnormal moving patterns.

8. The method of claim 5, wherein the step of continuously receiving comprises continuously receiving from the one or more video sensors an animal population density information at each area where the population of subjects resides.

9. The method of claim 1, wherein the step of generating an alert to prevent or control the disease comprises sending a text message, voice message, audio message, video message, data message and encrypted message.

10. The method of claim 1, wherein the step of comparing the information of the population of subjects with known disease symptom information comprises comparing the information of the population of subjects a historical data model of known disease symptom information.

11. The method of claim 1, wherein the initiating step comprises one or more of adding a chemical to a contaminated water source and sending medical equipment to an infected geographical region.

12. A system comprising:
a memory and a processor operatively coupled to the memory and configured to implement the steps of:
   continuously receiving, from two or more sensors positioned in a subject environment, information of a population of subjects, wherein the two or more sensors comprise one or more audio sensors and one or more motion sensors positioned along a route of travel of the subject population and one or more underwater sensors positioned in a water source located along the route of travel and wherein the information received from each of the two or more sensors is in a different data format;
   comparing the received information of the population of subjects with known disease symptom information, wherein the comparing further comprises comparing a first time period in which no event of interest has occurred to a second period of time in which one or more events of interest have occurred using a machine learning algorithm to determine a distinction between a type of event or a lack of event, and recognize a future event based on the distinction;
   in response to determining that the information of the population of subjects exceeds a pre-determined threshold alert level, generating an alert to prevent or control the disease; and
   initiating a response or action to inhibit, prevent, control or remedy the outbreak of the disease.

13. The system of claim 12, wherein the two or more sensors further comprise one or more additional sensors.

14. The system of claim 12, wherein the one or more audio sensors are one or more microphones.

15. The system of claim 13, wherein the one or more additional sensors comprise one or more of a video sensor, image sensor and color sensor.

16. The system of claim 12, wherein the continuously receiving comprises continuously receiving from the one or more audio sensors a coughing sound from the population of subjects.

17. The system of claim 12, wherein the continuously, receiving comprises continuously receiving from the one or more motion sensors movement patterns of the population of mammals in order to determine any abnormal moving patterns.

18. The system of claim 15, wherein the step of continuously, receiving comprises continuously receiving from the one or more video sensors an animal population density information at each area where the population of subjects resides.

19. The system of claim 12, wherein the step of generating an alert to prevent or control the disease comprises sending a text message, voice message, audio message, video message, data message and encrypted message.

20. A computer program product comprising a computer readable storage medium for storing computer readable program code which, when executed, causes a computer to:
   continuously receive, from two or more sensors positioned in a subject environment, information of a population of subjects, wherein the two or more sensors comprise one or more audio sensors and one or more motion sensors positioned along a route of travel of the subject population and one or more underwater sensors positioned in a water source located along the route of travel and wherein the information received from each of the two or more sensors is in a different data format;
   compare the received information of the population of subjects with known disease symptom information, wherein the comparing further comprises comparing a first time period in which no event of interest has occurred to a second period of time in which one or more events of interest have occurred using a machine learning algorithm to determine a distinction between a type of event or a lack of event, and recognize a future event based on the distinction;
   in response to determining that the information of the population of subjects exceeds a pre-determined threshold alert level, generate an alert to prevent or control the disease; and
   initiate a response or action to inhibit, prevent, control or remedy the outbreak of the disease.

* * * * *